(12) United States Patent
Nair et al.

(10) Patent No.: US 8,414,752 B2
(45) Date of Patent: *Apr. 9, 2013

(54) MULTILAYER CERAMIC $NO_x$ GAS SENSOR DEVICE

(75) Inventors: Balakrishnan G. Nair, Sandy, UT (US); Jesse Nachlas, Salt Lake City, UT (US)

(73) Assignee: EmiSense Technologies, LLC, San Juan Capistrano, CA (US)

( * ) Notice: Subject to any disclaimer, the term of this patent is extended or adjusted under 35 U.S.C. 154(b) by 828 days.

This patent is subject to a terminal disclaimer.

(21) Appl. No.: 12/610,973

(22) Filed: Nov. 2, 2009

(65) Prior Publication Data
US 2010/0096264 A1    Apr. 22, 2010

Related U.S. Application Data

(63) Continuation of application No. 11/182,278, filed on Jul. 14, 2005, now Pat. No. 7,611,612.

(51) Int. Cl.
*G01N 27/407* (2006.01)

(52) U.S. Cl.
USPC .......................... 204/426; 205/781; 205/785

(58) Field of Classification Search .................. 204/424, 204/426, 427; 205/781, 785
See application file for complete search history.

(56) References Cited

U.S. PATENT DOCUMENTS

| | | | | |
|---|---|---|---|---|
| 5,672,811 A | * | 9/1997 | Kato et al. | 73/31.05 |
| 7,611,612 B2 | * | 11/2009 | Nair et al. | 204/426 |
| 2005/0067282 A1 | * | 3/2005 | Cramer et al. | 204/424 |

\* cited by examiner

*Primary Examiner* — J. Christopher Ball
(74) *Attorney, Agent, or Firm* — Jeffrey T. Holman (57) ABSTRACT

A mixed potential $NO_x$ sensor apparatus for measuring the total $NO_x$ concentration in a gas stream is disclosed. The $NO_x$ sensing apparatus comprises a multilayer ceramic structure with electrodes for sensing both oxygen and $NO_x$ gas concentrations and includes screen-printed metallized patterns that function to heat the ceramic sensing element to the proper temperature for optimum performance. This design may provide advantages over the existing technology by miniaturizing the sensing element to provide potentially faster sensor light off times and thereby reduce undesired exhaust gas emissions. By incorporating the heating source within the ceramic sensing structure, the time to reach the temperature of operation is shortened, and thermal gradients and stresses are minimized. These improvements may provide increased sensor performance, reliability, and lifetime.

31 Claims, 9 Drawing Sheets

MULTILAYER CERAMIC NO$_x$ GAS SENSOR DEVICE

RELATED APPLICATIONS

This application is a continuation application of, and claims the benefit of U.S. patent application Ser. No. 11/182,278 filed on Jul. 14, 2005 now U.S. Pat No. 7,611,612, which application is related to and claims the benefit of U.S. patent application Ser. No. 11/137,693, of Balakrishnan Nair, Jesse Nachlas, and Michael Middlemas filed on May 25, 2005, and entitled "NO$_x$ Sensor Method and Device" and U.S. Provisional Patent No. 60/574,622 of Balakrishnan Nair, Jesse Nachlas, and Michael Middlemas filed on May 26, 2004, and entitled "NO$_x$ Gas Sensor Method and Device." Each of these applications is incorporated herein by reference in their entirety.

GOVERNMENT RIGHTS

This invention was made in part with government support under Grant Numbers 68-D-02-076 and 68-D-03-061 awarded by the United States Environmental Protection Agency. The Government has certain rights in the invention.

FIELD OF THE INVENTION

The present invention relates in general to the measurement of NO$_x$ gases in exhaust streams generated from the combustion of hydrocarbons, and more particularly, to the measurement of NO$_x$ gases in exhaust gas streams produced by the combustion of gasoline and/or diesel fuels.

BACKGROUND OF THE INVENTION

The composition of exhaust gases produced by the combustion of hydrocarbon fuels is a complex mixture of oxide gases (NO$_x$, SO$_x$, CO$_2$, CO, H$_2$O), unburnt hydrocarbon gases, and oxygen. Measurement of the concentration of these individual constituents of exhaust gases in real time can result in improved combustion efficiency and lower emissions of polluting gases. In some cases, the concentration of one gas may influence or control the concentration of a second gas. In these situations, it may be required to know the concentration of the first gas in order to measure the concentration of a second, or even third, gas accurately. Various devices have been proposed to operate as exhaust gas sensors that have the capability of measuring the gas concentration of two or more gases in an exhaust stream.

One NO$_x$ sensor known in the art is configured as a flat plate multilayer ceramic package designed to include two or more chambers. The first chamber has electrodes attached to an oxygen ion-conducting electrolyte membrane to form an oxygen pump for removing oxygen from a flow of gas entering the sensor. The first chamber also catalyzes the decomposition of NO$_2$ to NO and one-half O$_2$. The oxygen pump in the first chamber also removes the oxygen formed by this process. Thus, in theory, the only oxygen-containing gas that enters the second chamber is NO. The second chamber includes a NO decomposing element that removes the oxygen from the NO using a second oxygen pump. The electrical current produced by the transport of oxygen from the decomposition of NO in the second chamber is correlated to the concentration of NO.

A number of concerns affect the commercial application of this known NO$_x$ sensor. For example, when the NO$_x$ concentration to be detected is low, residual oxygen can cause significant interference. In addition to the above, the signal current produced by the sensor is very small, thus making it susceptible to interference from the electronic noise commonly found in an automobile. Also, the flow of exhaust gas monitored by such sensors typically has pulsations in its flow rate caused at least in part by engine cylinder firings. This impairs the ability of the oxygen pump to effectively remove all of the free oxygen and may result in measurement error. This device may also contain a small diffusion aperture used to limit the passage of gas into the measurement chambers. This structure has been demonstrated to be prone to clogging during use.

Another known NO$_x$ sensor utilizes a similar flat plate multilayer ceramic package design. There are a few significant differences in the operation principle for this sensor; namely, the sensor is a mixed potential type rather than amperometric, and the first chamber is used to convert NO to NO$_2$ and vice versa. It is well established that in mixed potential NO$_x$ sensors, the voltage signals generated from the gas species NO and NO$_2$ are of opposite sign. As a result, it is difficult to distinguish a meaningful voltage signal when both gases are present since cancellation may occur.

Some sensor designs have attempted to address this problem by utilizing a flat plate multilayer package design with two separate chambers built into the sensor. Attempts have also been made to convert all of the NO$_x$ gas species into a single species with the use of an electrochemical oxygen pump that pumps oxygen into the first chamber to attempt to convert all of the gas to NO$_2$. Other efforts conversely attempt to remove oxygen from the chamber and reduce all of the NO$_2$ to NO. This "conditioned" gas then passes into the second chamber where the NO$_x$ concentration is measured by the voltage signal generated from a mixed potential type sensor.

There are a number of limitations to this approach that have hampered the commercialization of this configuration. One significant concern is the reproducibility of the conversion system to completely convert all the NO$_x$ gases into a single species under varying gas concentration conditions. In addition, the oxygen pump conversion cell tends to degrade with time, further contributing to the issue of reproducibility. Because the effects of these concerns are magnified in the low concentration range, this measurement approach is not well suited for detecting low concentrations of NO$_x$ gases.

Additional drawbacks common to both of the sensor mechanisms discussed above stem from the fundamental design of the flat plate ceramic multilayer system. Response times tend to be slow because of the complexity of the device requiring gas to first enter through a diffusion port, be conditioned in a first chamber, and then to diffuse into a second chamber. Achieving rapid gas exchange that can keep up with the dynamic environment of the engine exhaust is difficult in these configurations. Also, the corrosive nature of the gas itself and the fact that it bears fine particulates may result in the clogging of the diffusion controlling port, or at the very least, changes in the gas flow dynamics with time. Finally, pulsations in gas flow rates due to cylinder firings and the electrical noise typical of automobiles make it difficult to control and monitor the low voltage and current circuits associated with these devices.

Thus, it would be an improvement in the art to provide alternative configurations for NO$_x$ sensing elements usable in a NO$_x$ sensor system designed to address these and other considerations. Such a device is provided herein.

BRIEF SUMMARY OF THE INVENTION

The present invention is directed to a method and design for constructing the NO$_x$ sensing element of a NO$_x$ sensor system previously described in patent application Ser. No. 11/137, 693, filed May 25, 2005, and incorporated by reference herein. The $NO_x$ sensing element comprises a multilayer ceramic structure with electrodes for sensing both oxygen and $NO_x$ gas concentrations and has included within the structure screen-printed metallized patterns that heat the ceramic sensing element to the proper temperature for optimum performance. This design provides advantages over the existing technology by miniaturizing the sensing element, which results in faster sensor light off times, thereby reducing undesired exhaust gas emissions. By incorporating the heating source within the ceramic sensing structure, the time to reach the temperature of operation is shortened and the thermal gradients and stresses are minimized, thus resulting in improved sensor performance, reliability and lifetime.

Other advantages and aspects of the present invention will become apparent upon reading the following description of the drawings and detailed description of the invention. These and other features and advantages of the present invention will become more fully apparent from the following figures, description, and appended claims, or may be learned by the practice of the invention as set forth hereinafter.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof that are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE INVENTION

The presently preferred embodiments of the present invention will be best understood by reference to the drawings, wherein like parts are designated by like numerals throughout. It will be readily understood that the components of the present invention, as generally described and illustrated in the figures herein, could be arranged and designed in a wide variety of different configurations. Thus, the following more detailed description of the embodiments of the multilayer ceramic $NO_x$ gas sensor device of the present invention, as represented in FIGS. 1A through 9, is not intended to limit the scope of the invention, as claimed, but is merely representative of presently preferred embodiments of the invention.

One embodiment of the present invention is a method for fabricating a multilayer ceramic structure to be used as a $NO_x$ sensing element. A complete $NO_x$ sensing apparatus was described in U.S. patent application Ser. No. 11/137,693, filed May 25, 2005, which is incorporated by reference herein in its entirety. The apparatus disclosed in that Application includes a sensor element. One of the features of the referenced $NO_x$ sensor apparatus is its ability to create two distinct temperature zones. One of these temperature zones is associated with the gas conditioning catalyst and oxygen sensor. A second of these temperature zones is associated with the mixed potential $NO_x$ sensing element. The present invention provides a novel sensor element for use in such sensing apparatus.

The sensor elements of the present invention may improve overall system performance by miniaturizing the ceramic sensing element and including multiple features within the miniaturized ceramic element. The ceramic sensor elements of the present invention may include a single sensing electrochemical cell, such as a $NO_x$ gas sensor, or may include at least two sensing electrochemical cells, such as oxygen and $NO_x$ gas sensors. The sensor elements of the invention additionally include at least one, and often two metallized patterns that function as "heater elements" to heat the entire ceramic structure when a voltage and current are applied to contact points of the metallized patterns.

By incorporating these heater elements into the ceramic structure of the sensor element, the heat transfer rate to the sensing electrodes is increased. This provides more rapid light off times for the sensor components of the sensor element. In addition to the above, thermal stresses due to rapid changes in temperature are minimized by optimization of the heater design pattern and the construction of the multilayer ceramic package. These features may result in improved lifetime performance and reliability of the sensor apparatus.

Several examples are provided below which discuss the construction, use, and testing of specific embodiments of the present invention. These embodiments are exemplary in nature and should not be construed to limit the scope of the invention in any way.

EXAMPLE 1

Figure 1A:
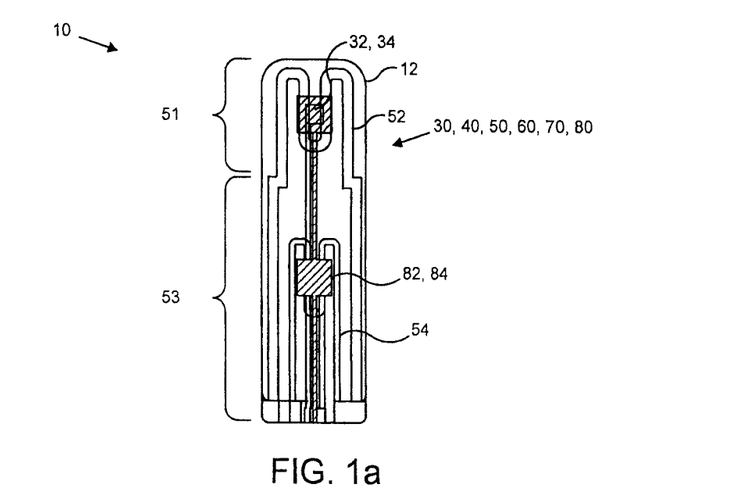
FIG. 1A is a schematic view of an embodiment of a planar multilayer ceramic sensing assembly of the present invention.

Referring first to FIG. 1A, the basic features of the multilayer gas sensor element 10 are illustrated. More specifically, the gas sensor element 10 is shown in a schematic view such that features of the individual layers 30, 40, 50, 60, 70, 80 used to make up the sensor body 12 are shown to overlap as they would in the completed sensor element 10. This view illustrates the relationship between features of the sensor element 10.

In the sensor element 10, the oxygen sensor 32 is positioned spatially near the heater element 52, but on an outer face of the element 10. A reference electrode 34 is positioned on an inner face of the oxygen sensor layer 30 in a substantially similar position. As a result, when viewed as in FIG. 1A, the oxygen sensor 32 and reference electrode 34 overlap. Similarly, the $NO_x$ sensor 82 is positioned spatially near the heater element 54 on an outer surface of the element 10. A reference electrode 84 is positioned on an inner face of the $NO_x$ sensor layer 80 in a substantially similar position. As a result, when viewed as in FIG. 1A, the $NO_x$ sensor 82 and the reference electrode 84 overlap. In some embodiments of the sensor elements of the invention, a gas sensor such as a $NO_x$ sensor that is insensitive to oxygen may be used. In such cases, the oxygen electrode may be omitted. Other sensors such as hydrocarbon sensors and/or CO sensors may be substituted in the place of the sensors described herein.

The heater 52 is configured to heat the oxygen sensor 32 to a temperature of from about 500° C. to about 900° C. and more preferably from about 650° C. to about 750° C. to create a first temperature zone 51. In some specific embodiments of the invention, the heater 52 heats the first temperature zone 51 encompassing the sensor 32 to a temperature of about 700° C. The heater 54 is configured to heat the $NO_x$ sensor to a temperature of from about 400° C. to about 600° C., and more preferably from about 450° C. to about 550° C. to create a second temperature zone 53. In some specific embodiments, the heater 54 heats the second temperature zone 53 encompassing the sensor 82 to a temperature of about 500° C. It should be noted that when installed in a sensing apparatus such as that disclosed in U.S. patent application Ser. No. 11/137,693, these heating elements 52, 54 may additionally provide heat to the catalyst, thus further improving the function of the apparatus as a whole.

Figure 1B:
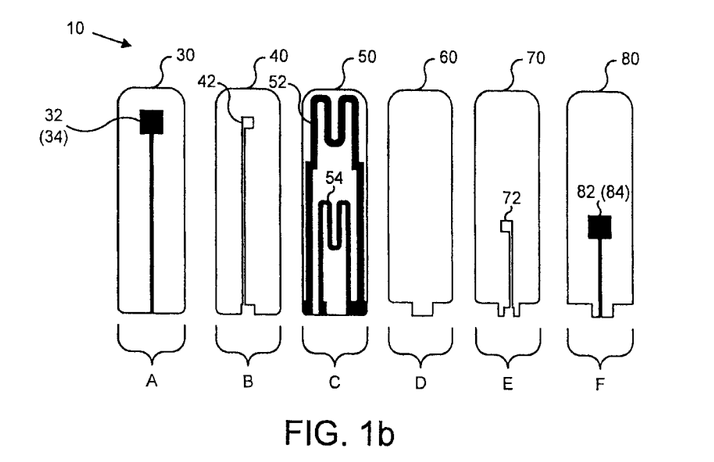
FIG. 1B illustrates each of the individual layers of the planar sensing assembly of the present invention, with the outermost layer being designated A, the next inward being designated B, the next C, the following D, the next E, and the lowest layer being designated F.
Figure 2:
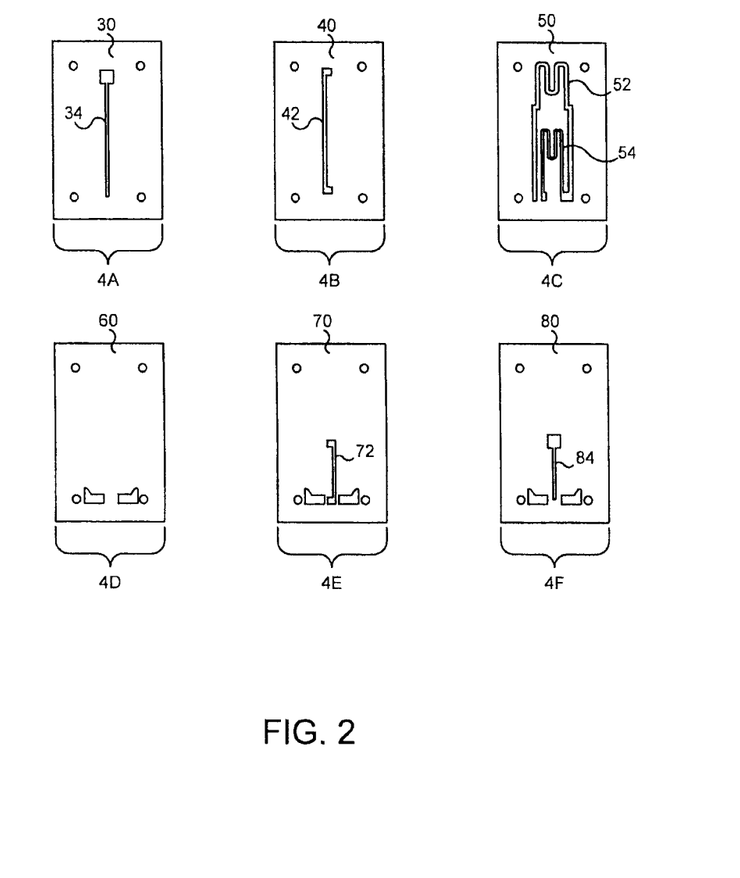
FIG. 2 illustrates the individual segments of green ceramic tape used to create the layers of the planar sensing assembly of the present invention, the appropriate segments showing electrode and heater patterns used in the device.

FIG. 1B provides a top view of each individual layer 30, 40, 50, 60, 70, and 80 of the sensor element 10 of the invention. Each of the layers 30, 40, 50, 60, 70, and 80 are initially produced from a green ceramic tape made using zirconia powder mixed with binders, solvents and plasticizers into a slurry that was suitable for tape casting. A variety of ion-conductive ceramic materials are known in the art and would be suitable for constructing conductive portions of the sensor body 12 of the sensor element 10 of the present invention, as would be understood by one of ordinary skill in the art. In some embodiments it may be advantageous to add a non-conductive or insulating region to the device. A variety of insulative ceramic materials are also known in the art and could be used for constructing the sensor body 12 of the sensor element 10 of the present invention, as would be understood by one of ordinary skill in the art. Following production of the zirconia slurry, the slurry was tape cast and dried prior to further manufacturing steps used in producing the final sensor element. Segments of the dried tape were cut to approximate shape using techniques common in the art.

As illustrated in FIG. 1B, an oxygen sensor layer 30 is provided for placement of an oxygen sensor electrode (not shown) and a reference electrode 34. The oxygen sensor electrode 32 is generally composed of platinum, but is not printed onto the oxygen sensor layer 30 until after the multilayer sensor 10 of FIG. 1A has been assembled and sintered (discussed in detail below). Although the oxygen sensor 32 may be printed onto the layer 30 prior to sintering in some circumstances, sintering of the sensor 32 may reduce its porosity, and hence, its sensitivity and effectiveness.

A first channel layer 40 is next provided, as illustrated in FIG. 1B. This layer 40 is cut to include a channel 42 extending into the sensor 10 to allow entry of the reference gas, which is typically air. The length and geometry of the channel 42 may be varied widely within the scope of the invention. The second channel layer 70 is also illustrated in FIG. 1B, the layer 70 including a channel 72 extending into the sensor 10. Channels 42, 72 allow air to enter the sensor 10 to reach reference electrodes 34 and 84 placed on interior surfaces of oxygen sensor layer 30 and $NO_x$ sensor layer 80, respectively. As with the channel 42 provided in the first channel layer 40, the channel 72 of the second channel layer 70 may be varied in size and geometry within the scope of the invention.

FIG. 1B further illustrates the heater layer 50 adapted to include heating elements 52, 54 that produce first and second temperature zones 51, 53. These heaters 52, 54 may be constructed to be independently-controlled, having distinct power sources; or to be controlled by the same power source and rendered capable of producing first and second temperature zones 51, 53 by varying the resistance of the individual heater 52, 54. Resistance may be varied in many ways, as understood by one of ordinary skill in the art, including increasing the length of the heater 52, 54. The heaters 52, 54 are positioned to be near the oxygen and $NO_x$ sensors 32, 72, on opposing sides of sensor body 12 making up the sensor 10 when it has been assembled. The electrodes provided for the heaters 52, 54 are screen printed and dried in an oven at 80° C. for 2 hours prior to assembly of the sensor 10. The individual layers 30, 40, 50, 60, 70, and 80 are shown overlaid with the patterns used to facilitate the screen-printing process (in the case of layers 30, 50, and 80) used to deposit the electrodes on each of the layers in FIG. 2, and to facilitate cutting of channels 42, 72 in layers 40 and 70.

Figure 3:
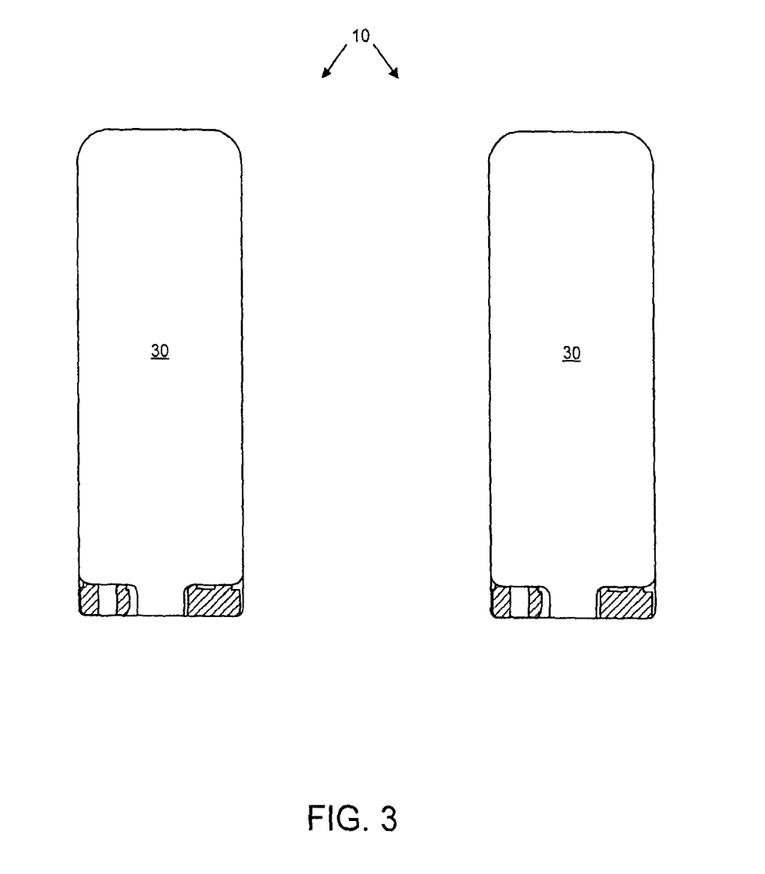
FIG. 3 shows a pair of assembled multilayer $NO_x$ sensors of the invention comprised of the layers illustrated in FIG. 2 having been stacked, laminated, and cut to their final shape in preparation for sintering.

After screen-printing the electrodes, the green ceramic layers 30, 40, 50, 60, 70, and 80 may be laminated together using a technique such as solvent bonding, heat lamination, or another technique known to one of ordinary skill in the art. In methods using heat lamination, the individual layers are pressed together using a lamination press. After lamination of the layers 30, 40, 50, 60, 70, and 80, the sensor elements 10 are cut to final shape using techniques known to those of ordinary skill in the art, and are then ready to be sintered. Two laminated and cut multilayer ceramic sensor packages 10 prepared for sintering are shown in FIG. 3.

Figure 4A:
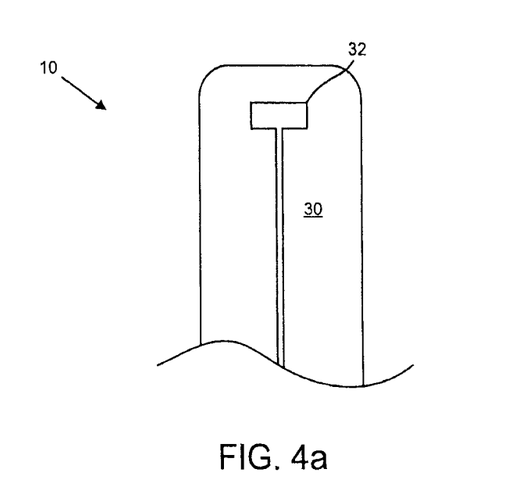
FIG. 4A is an isolated top view of a sintered multilayer $NO_x$ sensor according to the invention.
Figure 4B:
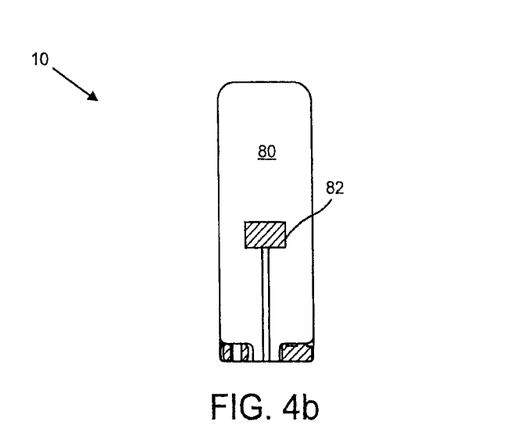
FIG. 4B is an isolated bottom view of a sintered multilayer $NO_x$ sensor according to the present invention.

The green laminated ceramic tape sensor package 10 was then sintered for two (2) hours at 1475° C. to produce the sensor element shown in FIGS. 4A and 4B. Following sintering, the ceramic sensor element structure 10 was coated with a platinum electrode for the oxygen sensor 32 on the side corresponding to the oxygen sensor layer 30 as schematically illustrated in FIGS. 1A and 1B. The opposing side of the ceramic structure 10 corresponding with original $NO_x$ sensor layer 80 was also coated with a composite electrode of $WO_3$/$ZrO_2$ to make up the $NO_x$ sensor 82. The $NO_x$ sensor electrode 82 is preferably placed on the sensor element 10 after sintering to prevent high-temperature chemical reaction with the zirconia in the green tape. After placement of the electrodes, the sensor element 10 was fired at a high temperature in the range of from about 800° C. to about 1000° C., and in some instances from about 850° C. to 950° C. to promote good adhesion of the oxygen sensor 32 and the $NO_x$ sensor 82 to the exterior of the sensor body 12.

In some embodiments of the sensor 10 of the present invention, the sensors 32, 82 may be mixed potential sensors constructed using a semi-conductive oxide material. In some specific embodiments, the semi-conductive oxide material may include at least one of the following: $WO_3$, $Cr_2O_3$, $Mn_2O_3$, $Fe_2O_3$, $TiO_2$, and $Co_3O_4$. In others, a multi-component oxide material may be used. The multi-component oxide material may be, for example, a spinel or perovskite. In some specific embodiments, the multi-component oxide material may be at least one of the following: $NiCr_2O_4$, $ZnFe_2O_4$, $CrMn_2O_4$, $LaSrMnO_3$, $LaSrCrO_3$, and $LaSrFeO_3$.

One of ordinary skill in the art would understand that the number and configuration of the layers 30, 40, 50, 60, 70, and 80 used to construct the gas sensor element 10 could be widely varied within the scope of the invention. Specifically, sensors 32, 82 or heaters 52, 54 could be placed in a variety of locations, including on opposing surfaces of single layers, to reduce the number of layers used to create the sensor body 12. Further, channels 42, 72 could be embossed or partially etched from a layer instead of being cut completely through. Other variations, including variations of electrode material, shape, and in some instances, placement could be made within the scope of the invention by one of ordinary skill in the art.

EXAMPLE 2

Figure 5:
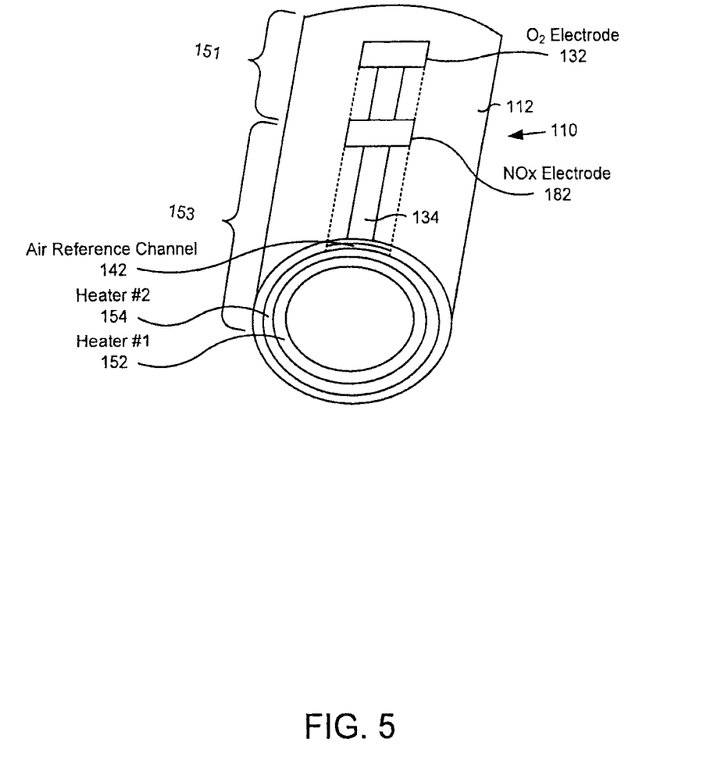
FIG. 5 is a plan view of another embodiment of the multilayer $NO_x$ sensors of the present invention having a tubular form that incorporates two heaters, an oxygen sensor, and a $NO_x$ sensor along with a shared air reference electrode.

While there are many advantages to the planar multilayer sensor element 10 characterized in Example 1 above, it may also be advantageous to utilize similar processing techniques to produce a multilayer sensor element 110 in the form of a tubular sensor body 112, as illustrated in FIG. 5. FIG. 5 shows a conceptual schematic of a multilayer tubular sensor element 110 which, like the sensor element 10 of FIGS. 1A-4B, incorporates two different heating zones 151, 153, along with both an oxygen sensing electrode 132 and a $NO_x$ sensing electrode 182. Both sensors 132, 182 share a common air reference electrode 134. It should be noted that the first and second heating zones 151, 153 illustrated in FIG. 5 are not in practice discrete zones, but are temperature regions with no concrete border separated instead by a continuum of intermediate temperatures.

Figure 6:
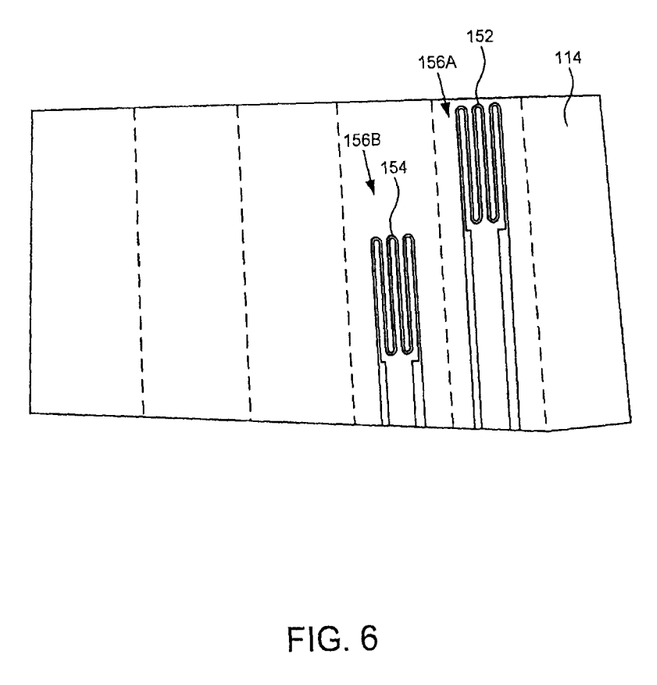
FIG. 6 illustrates the patterns used for screen printing heaters on unsintered zirconia tape for use in constructing the tubular sensor body.

To fabricate the tubular sensor element 110 illustrated in FIG. 5, the first step was to produce a ceramic tubular multilayer structure that contained two separate heaters 152, 154 to produce two different temperature zones 151, 153 associated with the electrodes 132, 182. To produce the ceramic structure, zirconia powder was mixed with binders, solvents and plasticizers into a slurry that was suitable for tape casting. The slurry was tape cast and dried to produce a green ceramic tape 114 with a thickness of approximately 0.015". FIG. 6 shows the green tape 114 having been cut to length and screen-printed with a platinum ink to form heater elements 152, 154. These heater elements 152, 154 are provided with distinct patterns 156A, 156B to produce two different temperature zones. The patterns 156A, 156B shown in FIG. 6 are exemplary only, and may be widely varied within the scope of the invention. Specifically, the size and length of the heater elements 152, 154 may be widely varied to provide differentially heated zones. In one example, the heater element 152 adapted to produce temperature zone 151 for the oxygen sensor 132 is longer and more tortuous to provide increased heat.

Figure 7:
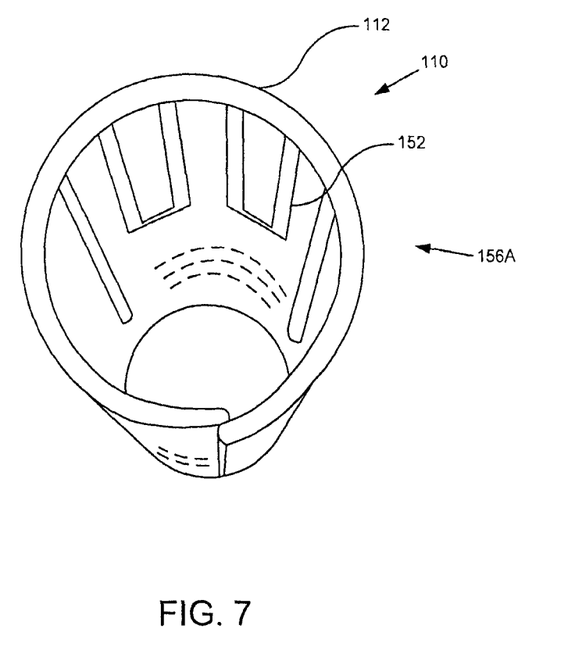
FIG. 7 is a perspective view of a sintered zirconia tubular $NO_x$ sensor constructed from the tape illustrated in FIG. 6.

As briefly mentioned above, FIG. 6 provides a picture of the green zirconia tape 114 that has been screen printed with platinum ink to produce the heaters 152, 154. After the platinum ink has properly dried, the green tape 114 is wrapped onto a tubular mandrel using terpineol to bond the wrapped layers of the tubular sensor body 112 together as they are wrapped around the mandrel. Once the tape 114 has been completely wrapped around the mandrel and dried it is then fired to 1475° C. for a 2-hour hold. FIG. 7 illustrates the sensor element 110 in the form of a sintered zirconia tube sensor body 112 showing the platinum heating pattern 156A on the inside surface of the sensor body 112. The sintered ceramic sensor element 110 was then ready for testing the performance of the heater elements 152, 154.

Figure 8:
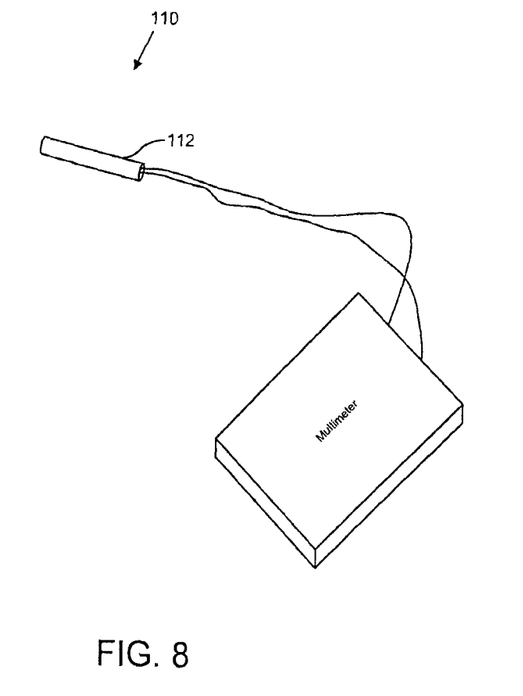
FIG. 8 illustrates a test setup for characterizing the performance of the heater of the tubular $NO_x$ sensor of FIG. 7.

The performance of the heater elements 152, 154 of the sensor element 110 was tested by first attaching lead wires to the contact points of the heaters 152, 154, and then attaching a DC power supply to each of the two heaters 152, 154. The heater elements 152, 154 performed as desired, producing 500° C. and 700° C. temperature zones. The heater elements 152, 154 were tested for over 500 hours. FIG. 8 illustrates the heaters 152, 154 being tested for heating rate and temperature profile. The heater patterns 156A, 156B used on heaters 152, 154, respectively, as shown in this example successfully produced the two different temperature zones 151, 153 required for the catalyst/oxygen sensor 132 and the $NO_x$ 182 sensor of the sensor element 110.

Figure 9:
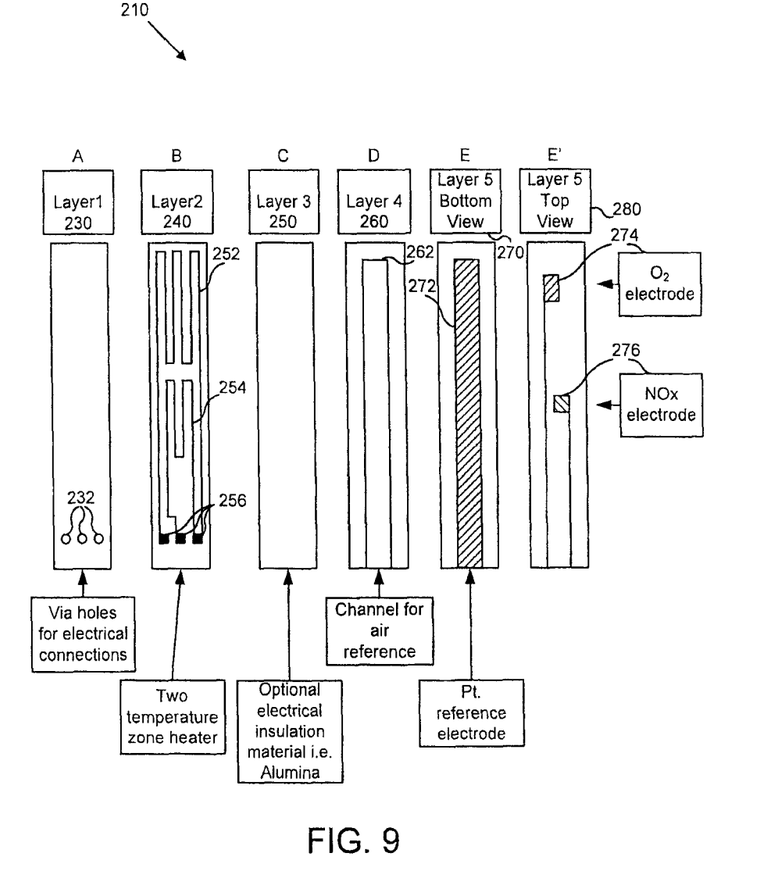
FIG. 9 illustrates the individual layers of another embodiment of the multilayer planar sensing assembly of the present invention, with an optional first layer being designated A, the next inward being designated B, the next C, the next D, and the final E, the final layer being shown twice, E showing its inward face and E' showing its outer face.

Another embodiment of the multilayer sensors of the present invention is illustrated schematically in FIG. 9. FIG. 9 illustrates the individual layers of another embodiment of the multilayer planar sensing assembly 210 of the present invention arrayed as in FIG. 1B. This embodiment may be assembled similarly to that described with reference to FIGS. 1A-4 discussed in greater detail above. The sensor 210 may first include an optional first layer 230. This layer 230 may include via holes 232 to allow access to the heaters 252, 254 of the heater layer 240. The heater layer 240 may be spaced from the channel layer 260 by an intermediate layer 250. The channel layer 260 may include a channel 262 to allow entry of air being channeled to the air reference electrode 272 found on an interior surface 274 of the sensor layer 270 illustrated in E. The oxygen-sensing and $NO_x$ sensing electrodes 274, 276, respectively, are placed as instructed above with reference to the embodiment of FIGS. 1A-4 on an exterior surface of the sensing layer 270 shown in E'.

While specific embodiments of the present invention have been illustrated and described, numerous modifications come to mind without significantly departing from the spirit of the invention, and the scope of protection is only limited by the scope of the accompanying claims.

The invention claimed is:

1. A gas sensor for detecting the concentration of a constituent in an exhaust gas, the sensor element comprising:
   a sensor body comprising a first sensing electrode and a second sensing electrode, and wherein the first and second sensing electrodes are configured to interact with an exhaust gas independently of each other;
   a first heater element integrated into the sensor body;
   a second heater element integrated into the sensor body, the first and second heater elements being placed and adapted to create first and second temperature zones associated with the first and second sensing electrodes, respectively.

2. The gas sensor of claim 1, wherein the sensor body comprises a plurality of layers.

3. The gas sensor of claim 1, wherein the first heater element is longitudinally displace from the second heater element along the sensor body.

4. The gas sensor of claim 1, wherein the first sensing electrode is located on an outside surface of the sensor body.

5. The gas sensor of claim 1, wherein the second sensing electrode is located on an outside surface of the sensor body.

6. The gas sensor of claim 1, wherein the first and second heater elements comprise separate electrical circuits that share a common ground potential electrical lead.

7. The gas sensor of claim 1, wherein the first and second heater elements comprise independently controlled electrical circuits.

8. The gas sensor of claim 1, wherein the first temperature zone is from about 500° C. to about 900° C.

9. The gas sensor of claim 8, wherein the first temperature zone is from about 650° C. to about 750° C.

10. The gas sensor of claim 9, wherein the first temperature zone is about 700° C.

11. The gas sensor of claim 1, wherein the second temperature zone is from about 400° C. to about 600° C.

12. The gas sensor of claim 11, wherein the second temperature zone is from about 450° C. to about 550° C.

13. The gas sensor of claim 12, wherein the second temperature zone is about 500° C.

14. The gas sensor of claim 1, further comprising a metallic shared air reference electrode.

15. The gas sensor of claim 14, wherein the metallic shared air reference electrode is exposed to atmospheric air containing about from about 15% to about 25% oxygen.

16. The gas sensor of claim 15, wherein the metallic shared air reference electrode is exposed to atmospheric air containing about 21% oxygen.

17. The gas sensor of claim 14, wherein the metallic shared air reference electrode comprises a metal selected from the group consisting of platinum, silver, gold, rhodium or any combination thereof.

18. The gas sensor of claim 1, further comprising a sealed metal/metal oxide reference electrode.

19. The gas sensor of claim 18, wherein the sealed metal/metal oxide reference electrode comprises a Ni/NiO electrode.

20. The gas sensor of claim 1, wherein at least one of the first sensing electrode and the second sensing electrode is a mixed potential electrode.

21. The gas sensor of claim 1, wherein at least one of the first sensing electrode and the second sensing electrode comprises a semi-conductive oxide material.

22. The gas sensor of claim 21, wherein the semi-conductive oxide material comprises at least one material chosen from $WO_3$, $Cr_2O_3$, $Mn_2O_3$, $Fe_2O_3$, $TiO_2$, and $Co_3O_4$.

23. The gas sensor of claim 1, wherein at least one of the first sensing electrode and the second sensing electrode comprises a multi-component oxide material.

24. The gas sensor of claim 23, wherein the multi-component oxide material comprises at least one of a spinel and a perovskite.

25. The gas sensor of claim 23, wherein the multi-component oxide material comprises a material chosen from $NiCr_2O_4$, $ZnFe_2O_4$, $CrMn_2O_4$, $LaSrMnO_3$, $LaSrCrO_3$, and $LaSrFeO_3$.

26. The gas sensor of claim 1, wherein the first sensing electrode is selected from the group consisting of $NO_x$-sensing electrodes, oxygen-sensing electrodes, hydrocarbon-sensing electrodes, $SO_2$-sensing electrodes, and CO-sensing electrodes.

27. The gas sensor element of claim 1, wherein the second sensing electrode is selected from the group consisting of $NO_x$-sensing electrodes, oxygen-sensing electrodes, hydrocarbon-sensing electrodes, $SO_2$-sensing electrodes, and CO-sensing electrodes.

28. The gas sensor element of claim 1, wherein the sensor body has a generally planar configuration.

29. The gas sensor element of claim 1, wherein the sensor body has a generally tubular configuration.

30. A gas sensor element for detecting the concentration of a gas constituent in an exhaust gas, the sensor element comprising:
a multilayer ceramic sensor body comprising a first sensing electrode that generates a voltage signal that is a function of the concentration of a first gas constituent being measured, said first gas constituent comprising NO or $NO_2$, and a second sensing electrode that generates a voltage signal that is a function of the concentration of a second gas constituent being measured, wherein the first and second sensing electrodes are configured to interact with said first and second gas constituents independently of each other;
a metallic shared air reference electrode;
a first heater element integrated into the ceramic body; and
a second heater element integrated into the ceramic body, the first and second heater elements being placed and adapted to create first and second temperature zones.

31. A gas sensor element for detecting the concentration of a gas constituent in an exhaust gas, the sensor element comprising:
a sensor body including a first sensing electrode that generates a voltage signal that is a function of the concentration of a first gas constituent being measured, said first gas constituent comprising NO or $NO_2$;
a second sensing electrode that generates a voltage signal that is a function of the concentration of a second gas constituent being measured, wherein the first and second sensing electrodes are configured to interact with said first and second gas constituents independently of each other;
a metallic shared air reference electrode, wherein the metallic shared air reference electrode is composed of a metal selected from the group consisting of platinum, silver, gold, rhodium or any combination thereof;
a first heater element integrated into the ceramic body; and
a second heater element integrated into the ceramic body, the first and second heater elements being placed and adapted to create first and second temperature zones;
wherein the first temperature zone is from about 650° C. to about 750° C., and wherein the second temperature zone is from about 450° C. to about 550° C.

* * * * *